US00PP10739P

United States Patent [19]

Lapins et al.

[11] Patent Number: Plant 10,739

[45] Date of Patent: Dec. 29, 1998

[54] APPLE TREE NAMED 'CRESTON'

[75] Inventors: Karl O. Lapins, Kelowna; W. David Lane, Summerland, both of Canada

[73] Assignee: Okanagan Plant Improvement Co. Ltd.

[21] Appl. No.: 879,122

[22] Filed: Jun. 19, 1997

[51] Int. Cl.[6] ..... A01H 5/00

[52] U.S. Cl. ..... Plt./34.1

[58] Field of Search ..... Plt./34.1

*Primary Examiner*—Howard J. Locker
*Assistant Examiner*—Melissa L. Kimball

[57] ABSTRACT

A new and distinct variety of apple tree from a controlled cross of 'Golden Delicious' and 'NJ 381049' is described. The variety is distinguished by its large ellipsoid shaped fruit with skin of broad orange/red stripes on a green/yellow ground and by the texture and taste of the creamy yellow flesh which is very juicy, sweet crisp and firm. The variety was named 'Creston' 1997.

3 Drawing Sheets

Background Of The Invention

This invention relates to apple trees and particularly to a seedling apple tree from a controlled cross made by the Pacific Agri-Food Research Centre Summerland apple breeding program located at Summerland, British Columbia, Canada. The Agriculture and Agri-Food Canada research facility at Summerland was established in 1914. Originally called the Dominion Experimental Farm at Summerland, the name was changed to the Summerland Research Station in 1959, the Summerland Research Centre in 1994 and to the Pacific Agriculture Agri-Food Research Centre Summerland in 1996. The tree fruit breeding program was established in 1924 to provide new varieties for the tree fruit industry of British Columbia, Canada, and the world. The breeding program at Summerland has produced several tree fruit varieties including 'Spartan', 'Summerred' and 'Sunrise' apples (all unpatented varieties) and 'Van', 'Lapins' and 'Sweetheart' cherries. The tree fruit breeders typically produce several thousand hybrid seedlings each year. Under the direction of the breeder the technician, as part of his duties, propagates the seedlings, by budding onto rootstocks, to induce earlier fruiting, in "seeding" fields. Upon fruiting, the varieties are evaluated for appearance, taste, texture, harvest indices, and disease susceptibility, and growth habit of the tree in the field. Promising seedlings are propagated, in replications of 4 to 6 trees, by budding or grafting onto rootstocks and planted out as second selections in variety evaluation plots. The reproductions are evaluated for varietal stability, disease susceptibility, and fruit and tree quality. The most promising selections are re- propagated and planted out in randomized evaluation plots complete with reference varieties (commercial varieties). Upon fruiting, selections are evaluated for varietal stability in the field, and for taste, texture and appearance of the fruit, and conducting "in-house" sensory evaluation panels. The new varieties are compared to reference varieties to establish uniqueness. The present invention relates to the new and distinct variety of apple tree named 'Creston'. 'Creston' originated from a controlled cross of 'Golden Delicious'×'NJ 381049' (unpatented) in 1966. The cross was made and the seed collected by Dr. K. O. Lapins while on a work project at Rutgers University in 1966. The seedling was planted at Summerland in 1967. The new variety was re-propagated (by budding) onto rootstocks in 1969, and given the breeders reference number '8M-15-10'. In 1976 Dr. W. David Lane was responsible for two-reproductions being made by budding and being planted in second selection variety test plots in 1977. The re-productions showed no variations from the original tree. '8M-15-10' was further re-propagated in 1986 and established into another second selection block in 1987. In 1992 four trees were planted in a randomized evaluation trial block complete with the reference varieties 'Fuji' (unpatented) and 'Royal Gala' (U.S. Plant No. 4121) sensory panels began in 1995. Grower panels began in 1995. '8M-15-10' was named 'Creston' in 1997.

Distinguishing Characteristics

'Creston' is a large apple averaging 7.8 cm in diameter and 220 to 280 grams in weight. The fruit has an ellipsoid shape, somewhat similar to 'Fuji', but more elongated with slight ribbing and a moderately deep calyx and stem end. The skin has less than 65% orange/red stripes over a yellow/green background with non-prominent lenticels. The flesh is creamy yellow in color and very juicy. 'Creston' has a sweet sub-acid taste, averaging 13% to 14.5% soluble solids and 455-700 milligrams of titratable acids per 100 grams of juice at harvest. The fruit is very crisp and firm in texture. The variety has been rated very highly in sensory evaluation panels held at the Pacific Agri-Food Research Centre. Initial storage assessments indicate the'Creston'stores for 2 months on 0°C. air storage and 4 to 5 months in controlled atmosphere (CA) storage. The tree habit is moderately vigorous and spreading.

Parent plants: 'Golden Delicious' ×'NJ 381049'.

'Golden Delicious' is the seed parent and 'NJ 381049' is the pollen parent.

'Golden Delicious' was developed from a chance seedling discovered in Clay Creek, W. Va. by Andrew H. Mullins.

'NJ 381049' was a selection of unknown parentage from the breeding program at Rutgers University.

Summary Of The Invention

The new and distinct variety of Malus fruiting apple tree 'Creston' was bred at Rutgers University in 1966 and the resulting seedling was planted at the Pacific Agri-Food Research Centre Summerland, British Columbia, Canada in 1969. The variety has been established and is being maintained at the research facility. Evaluations began in 1977. The variety is stable with no variations occuring and demonstrates significant differences from its parents in the 'Creston' is a large apple with a distinct ellipsoid shape, a moderately deep calyx and stem end and a skin color of less than 65% prominent orange/red stripes on a yellow/green background. The flesh is creamy yellow in color, very juicy, with a sweet subacid taste. The fruit has ben rated as having very crisp and firm texture. The tree is large and has a spreading growth habit, similar to 'Jonagold' (unpatented). The variety matures approximately the first week of October at Summerland, 'Creston' was first propagated, by budding, in 1969 and a single propagation was planted in a "seedling" evaluation plot. In 1976 four trees were made, (by budding), and planted out in the second variety test plots. The reproductions showed no variations from the original tree. '8M 15-10' was re-propagated by budding in 1982, and established in a randomized evaluation trial plot complete with the reference varieties 'Jonagold' and 'Royal Gala'. Sensory panels were conducted in 1995 and 1996.

Brief Description Of The Drawings

The accompanying photographs show the mature fruit, a typical limb, leaves and fruit, and tree habit of 'Creston'

The photograph on sheet 1 shows the typical mature fruit positioned to display stem end, calyx end and side view. The photograph also displays a cross-sectional view to reveal the internal arrangement of the core, seeds and locules and a longitudinal section to show the eye basin, stem bowl, core, and the color of the flesh and seeds.

The photographs on sheet 2 each illustrate the mature fruit prior to harvest; the photograph on sheet 3 illustrates the bearing and tree habit.

Trials And Evaluations:

A seedling resulting from a controlled cross made in 1966 was asexually reproduced in 1969 by budding and given the breeders reference number '8M-15-10'. '8M-15-10' was reproduced and planted in cultivated variety blocks, complete with standards at the Pacific Agri-Food Research Centre Summerland orchands in 1976. The reproductions have shown 'Creston' to be stable with no variations occurring. The variety has been observed and evaluated sinced first fruiting. Test plots established at PARC Summerland consisting of 4 trees of 'Creston'('8M-15-10') were established in 1987. The variety was compared to the reference variety 'Jonagold' and of approximately the same age and planted in the same area. Controlled grower trials, under test agreements, have been established in British Columbia. The tree is of medium vigor and is precocious, but tends to be biennial. 'Creston' does not show and unusual susceptibility to any diseases including mildew, fireblight and apple scab.

'Creston' was tested in sensory evaluation panels in 1995 and 1996. Sensory evaluation panels consist of 10 to 12 trained panelists. About 10 apple varieties, including 1 or 2 standards, are rated per session on a hedonic (liking) scale for texture, flavor and appearance. In addition. panelists use a sensory scale to rate the intensity of crispness, hardness, juiciness, sourness, sweetness and aromatics. All ratings are on a scale of 0 to 9, with 0 being a low rating and 9 being a high rating. The standards used in sensory evaluation panels were 'Fuji' and 'Gala' in 1995 and 1996. 'McIntosh' was included in 1996 panels as a comparator. Panelists rated 'Creston' and 'Fuji' as equally acceptable in appearance, texture and flavor in 1995. On sensory scales 'Creston' was rated less firm and less hard than 'Fuji' but as juicy, sweet, sour, and aromatic. 'Creston' was rated significantly higher than 'McIntosh' in flavor and texture on a hedonic scale in 1996, and significantly higher in crispness, hardness, and sweetness on sensory scales. In 1996 'Creston' rated equal to 'Royal Gala' in texture and taste, and less acceptable in appearance on hedonic scales. On sensory scales 'Creston' rated less hard than 'Royal Gala' and equal to 'Royal Gala' in crispness, sweetness, aroma, juice, and sourness. 'Creston' requires multiple-picks to achieve acceptable color. Initial storage assessments indicate the fruit of 'Creston' will store for 2 months in 0°C. air storage and 4 to 5 months in controlled atmosphere (CA) storage.

Botanical Description Of The Plant

'Creston'

Genus: Malus.
Species: ×*domestica*.
Market class: Dessert.
Parentage: 'Golden Delicious' ×'NJ 381049'.

'Golden Delicious'

Genus: Malus.
Species: ×*domestica*.
market class: Dessert.
Parentage: Naturally occuring chance seedling.

'NJ381049'

Genus: Malus.
Species: ×*domestica*.
Market class: Unknown.
Parentage; Unknown.

The following is a detailed description of the new variety, with color terminology in accordance with The Royal Horticultural Society (RHS) Colour Chart, except where general color terms of ordinary dictionary significance are suitable.

Promological Characteristics 'Creston'

Fruit end use:

Growth characteristics:

*Tree.*—Trees observed were on M26 rootstocks planted in 1987. Vigor: Intermediate. Habit: Upright spreading. Branch frequency: Medium. Branch strength: Intermediate. Angle of bearing branches: 50 to 90 degrees. Predominance of bearing: Spurs.

Shoot characteristics: Measurements are the mean of ten one year old shoots done in 1996.

*Pubescence (on upper half).*—Weak.
*Shine of bark.*—Medium.
*Mean diameter (center of middle internode.*—5 mm.
*Mean internode length.*—29 mm.
*Number of lenticels (middle third of shoot).*—Medium to many.
*Size of lenticels.*—Medium.
*Predominant color (on sunny side).*—Reddish-brown.
*Position of bud on shoot.*—Appressed.
*Shape of bud.*—Pointed.

Flower characteristics: Measurements are the mean of 10 flowers.

*Type.*—Single.
*Size (pressed flat).*—55 mm.
*Color of bud (balloon stage).*—60B/155D (R.H.S.).
*Bud burst.*—Early, before 'Jonagold'.
*Petal shape.*—Broad elliptic.
*Petal margins.*—Overlapping.

Leaf characteristics: Measurements are the mean of 10 fully expanded leaves $4^{th}$ to $6^{th}$ from top of shoot.

*Shape at cross section.*—Concave.
*Pubescense of upper side.*—Weak.

*Color upper side.*—139A (R.H.S.).
*Anthocyanin coloration.*—None.
*Orientation.*—Outwards.
*Leaf apex.*—Acuminate.
*Leaf margins.*—Serrate.
*Leaf length.*—Mean: 91 mm. Range: 75 to 109 mm.
*Leaf width.*—Mean: 91 mm. Range: 46 to 75 mm.
*Blade ratio (length/width).*—1.5.
*Petiole length.*—Mean: 26 mm, Range: 19 to 36 mm.
*Ratio of leaf length to petiole length.*—3.50.
*Glossiness of upper side.*—Medium to strong.
*Pubescence on lower side.*—Pubescent.
Stipule length.—Mean: 14mm. Range: 12 to 20 mm.

Fruit characteristics: Measurements are the mean of 10 mature fruit.

*Size (diameter).*—79 mm.
*Average fruit weight.*—220 to 280 grams.
*Shape.*—Ellipsoid.
*Symmetry (side view).*—Symmetrical.
*Ribbing.*—Present.
*Prominence of ribbing.*—Very slight.
*Prominence of crowning.*—Weak to medium.
*Aperture of eye.*—Open.
*Depth of eye basin.*—15 mm.
*Width of eye basin.*—39 mm.
*Sepal spacing.*—Overlapping.
*Thickness of stalk.*—2.4 mm.
*Depth of stalk cavity.*—17 mm.
*Stalk cavity width.*—31 mm.
*Stalk length.*—30 mm.
*Surface.*—Smooth.
*Bloom of skin.*—Absent.
*Waxiness of skin.*—Waxy.
*Translucency of skin.*—Absent.
*Ground colour.*—Green/yellow.
*Overcolor of skin.* —46 B (R.H.S.).
*Amount of overcolor of skin.*—less than 65%.
*Type of overcolor.*—Streaked and solid.
*Amount of russet.*—Medium.
*Position of russet.*—Cheeks and stem bowl.
*Size of lenticels on fruit.*—Small to medium.
*Prominence of lenticels.*—Slight to medium.
*Color of flesh.*—Cream (R.H.S. not available).
*Distinctness of core line.*—Weak.
*Aperture of locules.*—Half open.
*Setting (yield efficiency).*—Good.
*Maturity date at Summerland, B.C.*—Early October.
*Seed color at maturity.*—Dark brown.
*Juiciness.*—Very juicy.
*Soluble solids.*—13% to 14 %.
*Titratable acids at harvest.*—450-700 mg malic acid per 100 ml juice.
*Flesh firmness (penetrometer).*—14 –15 lbs. (at harvest).
*Browning of flesh (1 hr. after cutting).*—Weak.

Storage life of fruit:

*Air.*—2 months.
*Controlled atmosphere.*—4 to 5 months.

We claim:

1. A new and distinct variety of apple tree, originating from a controlled cross of 'Golden Delicious' ×'NJ 381049', substantially as illustrated and described. herein which is most similar to 'Jonagold' and characterized as to novelty by its distinct elllipsoid shape, moderately deep calyx and stem end and a skin color of 30% to 40% prominent orange/red stripes on a yellow/green background and the unique combination of taste, texture and juiciness which are different from other dessert quality apples.

* * * * *

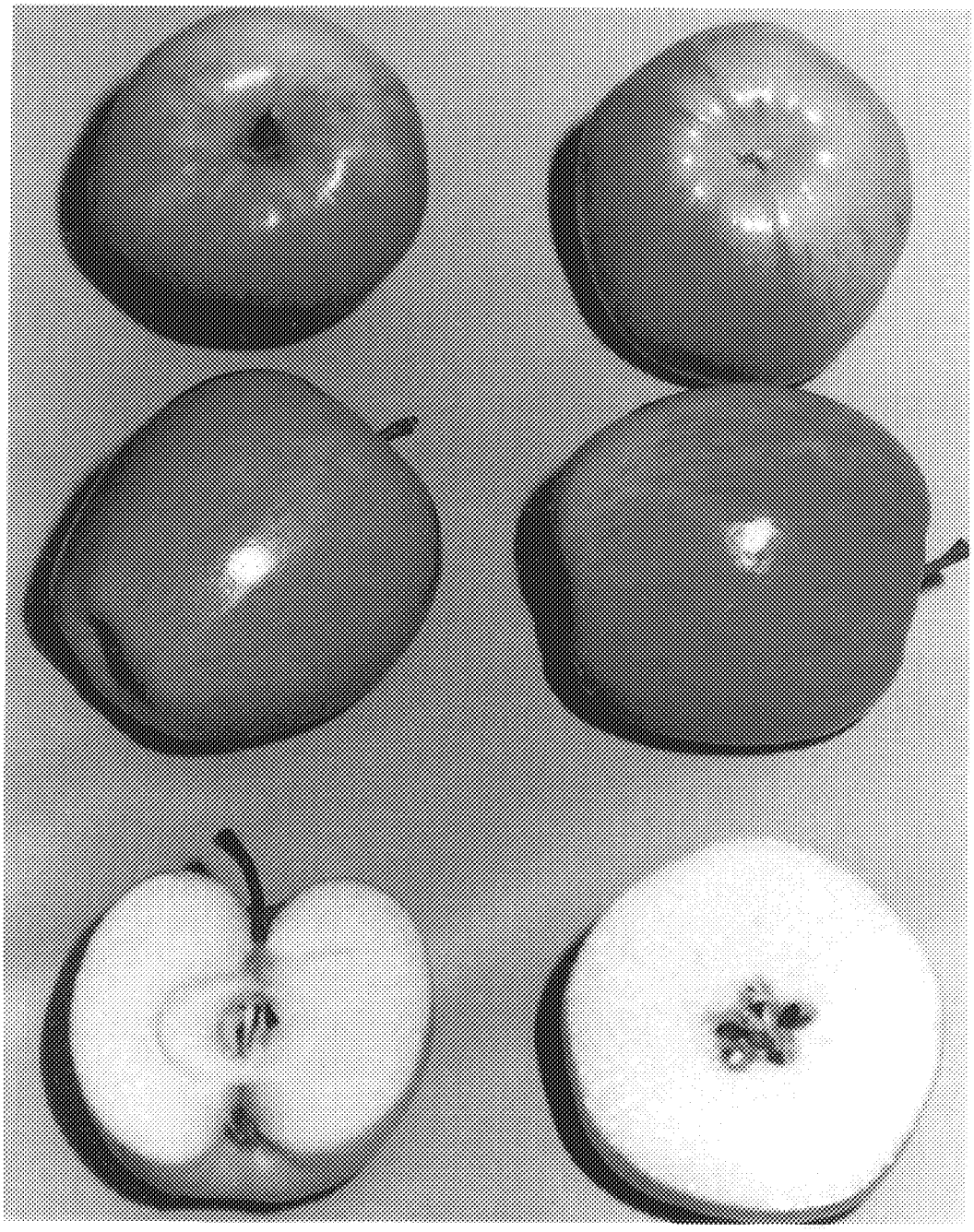

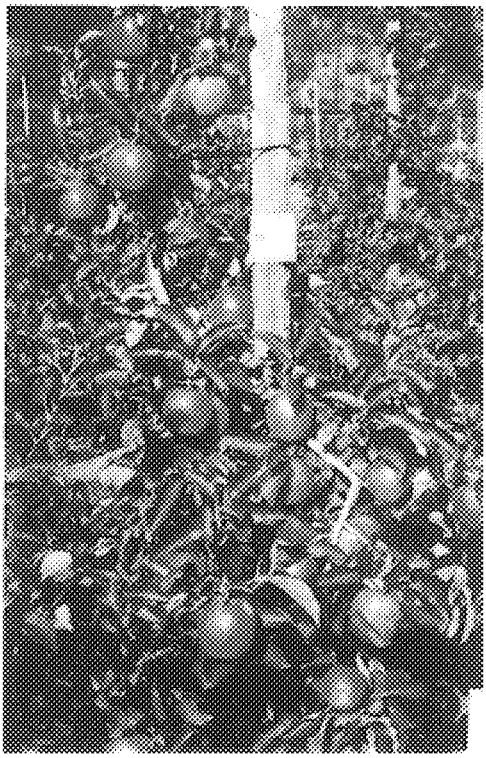

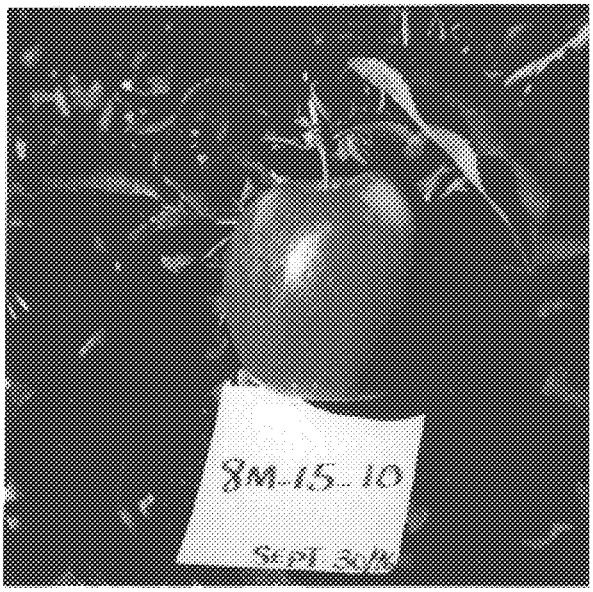
8M-15-10
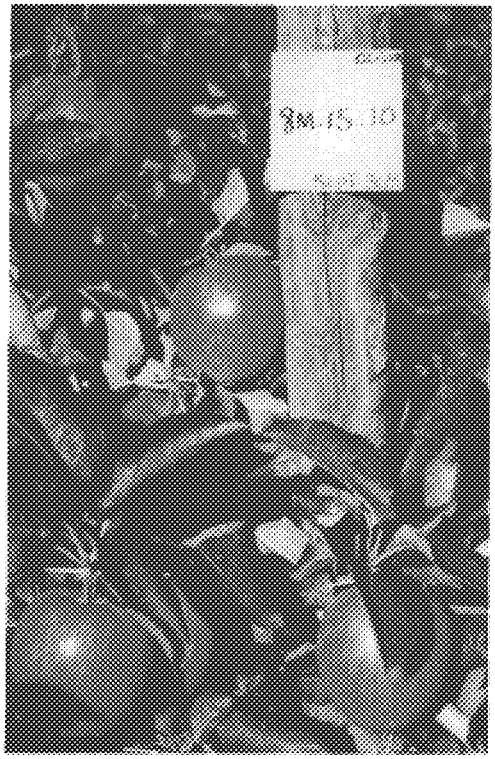
8M-15-10